United States Patent
Kumar KN et al.

(10) Patent No.: US 9,153,051 B2
(45) Date of Patent: Oct. 6, 2015

(54) VISUALIZATION OF PARALLEL CO-ORDINATES

(71) Applicants: Ashok Kumar KN, Bangalore (IN); Anil Babu Ankisettipalli, Bangalore (IN)

(72) Inventors: Ashok Kumar KN, Bangalore (IN); Anil Babu Ankisettipalli, Bangalore (IN)

(73) Assignee: BUSINESS OBJECTS SOFTWARE LIMITED, Dublin (IE)

( * ) Notice: Subject to any disclaimer, the term of this patent is extended or adjusted under 35 U.S.C. 154(b) by 413 days.

(21) Appl. No.: 13/781,762

(22) Filed: Mar. 1, 2013

(65) Prior Publication Data

US 2014/0247267 A1 Sep. 4, 2014

(51) Int. Cl.
*G06T 11/20* (2006.01)
*G06F 19/26* (2011.01)

(52) U.S. Cl.
CPC .............. *G06T 11/206* (2013.01); *G06F 19/26* (2013.01)

(58) Field of Classification Search
None
See application file for complete search history.

(56) References Cited

U.S. PATENT DOCUMENTS

| | | | |
|---|---|---|---|
| 5,546,516 A * | 8/1996 | Austel et al. | 345/440 |
| 5,917,500 A | 6/1999 | Johnson et al. | |
| 6,034,697 A | 3/2000 | Becker | |
| RE36,840 E | 8/2000 | Mihalisin et al. | |
| 6,362,823 B1 | 3/2002 | Johnson et al. | |
| 6,373,483 B1 * | 4/2002 | Becker et al. | 345/419 |
| 6,750,864 B1 | 6/2004 | Anwar | |
| 7,051,025 B2 | 5/2006 | Kan et al. | |
| 7,272,786 B1 | 9/2007 | McCullough | |
| 7,571,129 B2 | 8/2009 | Ebert | |
| 8,259,114 B2 | 9/2012 | Schwarzmann | |
| 8,386,466 B2 | 2/2013 | Park et al. | |
| 8,694,539 B2 | 4/2014 | Soderstrom et al. | |
| 2004/0148578 A1 | 7/2004 | McConaghy et al. | |
| 2008/0055313 A1 | 3/2008 | Noppens | |
| 2013/0147828 A1 | 6/2013 | Vogel et al. | |
| 2013/0300743 A1 | 11/2013 | Degrell et al. | |

OTHER PUBLICATIONS

Heinrich et al. "State of the art of parallel coordinates." STAR Proceedings of Eurographics 2013 (2013): 95-116.*
Novotny et al. "Outlier-preserving focus+ context visualization in parallel coordinates." Visualization and Computer Graphics, IEEE Transactions on 12.5 (2006): 893-900.*

(Continued)

*Primary Examiner* — Ke Xiao
*Assistant Examiner* — Jed-Justin Imperial (57) ABSTRACT

Parallel co-ordinates associated with a business scenario represent underlying data of the business scenario. Based upon associated categorical variables, the parallel co-ordinates are divided into a plurality of segments. Each segment includes a pair of continuous variables represented as a pair of axes of the parallel co-ordinates. The pairs of axes of the parallel co-ordinates are fragmented to generate bi-variant bins. The bi-variant bines include continuous values corresponding to each fragment of the pair of axis. An associated backend database is queried to determine aggregated tuples of continuous values between each bi-variant bin of the corresponding pair of axes. Based on the aggregated tuples, a statistical visualization of the aggregated tuples between the bi-variant bins for the axes is generating. The statistical visualization includes a distribution of the tuples for the plurality of segments corresponding to the parallel co-ordinates.

18 Claims, 9 Drawing Sheets

(56) References Cited

OTHER PUBLICATIONS

Inselberg et al. "Parallel coordinates: survey of recent results."IS&T/SPIE's Symposium on Electronic Imaging: Science and Technology. International Society for Optics and Photonics, 1993.*

Ying-Huey Fua, Matthew O. Ward, Elke A. Rundensteiner; Hierarchical Parallel Coordinates for Exploration of Large Datasets; VIS 1999 Proceedings of the conference on Visualization 1999; pp. 43-50; IEEE Computer Society Press Los Alamitos, CA, USA; (http://dl.acm.org/citation.cfm?id=319355).

Ben Shneiderman; Extreme Visualization: Squeezing a Billion Records into a Million Pixels; SIGMOD Proceedings of the 2008 ACM SIGMOD International conference on Management of data ; Jun. 9-12, 2008; pp. 3-12; ACM New York, NY, USA; (http://dl.acm.org/citation.cfm?id=1376618).

* cited by examiner

| CATEGORICAL VARIABLE | CONTINUOUS VARIABLE | CONTINUOUS VARIABLE | CONTINUOUS VARIABLE | CONTINUOUS VARIABLE |
|---|---|---|---|---|
| PLANT TYPE | SEPAL WIDTH | SEPAL LENGTH | PETAL LENGTH | PETAL WIDTH |
| SETOSA | 5.1 | 3.5 | 1.4 | 0.2 |
| SETOSA | 4.9 | 3.0 | 1.4 | 0.2 |
| SETOSA | 4.7 | 3.2 | 1.3 | 0.2 |
| SETOSA | 4.6 | 3.1 | 1.5 | 0.2 |
| SETOSA | 5.0 | 3.6 | 1.4 | 0.2 |
| VERSICOLOR | 7.0 | 3.2 | 4.7 | 1.4 |
| VERSICOLOR | 6.4 | 3.2 | 4.5 | 1.3 |
| VERSICOLOR | 6.9 | 3.1 | 4.9 | 1.5 |
| VERSICOLOR | 5.5 | 2.3 | 4.0 | 1.3 |
| VERSICOLOR | 6.5 | 2.8 | 4.6 | 1.5 |
| VIRGINICA | 6.3 | 3.3 | 6.0 | 2.5 |
| VIRGINICA | 5.8 | 2.7 | 5.1 | 1.9 |
| VIRGINICA | 7.0 | 3.0 | 5.9 | 2.1 |
| VIRGINICA | 6.3 | 2.9 | 5.6 | 1.8 |
| VIRGINICA | 6.5 | 3.0 | 5.8 | 2.2 |

| AGGREGATION TABLE 600 | | |
|---|---|---|
| SEPAL WIDTH | SEPAL LENGTH | NO. OF RECORDS |
| 7 | 5 | 0 |
| 7 | 4.9 | 0 |
| 7 | 4.8 | 0 |
| . | . | . |
| . | . | . |
| . | . | . |
| 6.5 | 3 | 1 |
| . | . | . |
| 6.5 | 2.8 | 1 |
| . | . | . |
| 5.1 | 2.8 | 1 |
| . | . | . |
| 5 | 2.7 | 1 |
| . | . | . |
| 4.9 | 3 | 1 |
| . | . | . |

VISUALIZATION OF PARALLEL CO-ORDINATES

TECHNICAL FIELD

The field generally relates to computer systems and software and more particularly to methods and systems to generate a visualization of parallel co-ordinates.

BACKGROUND

A parallel co-ordinate is a method of visualizing and analyzing multivariate data. Records of data are generally plotted as a line in the parallel co-ordinate. Since records are plotted as a line, handling an enormous amount of data is a cumbersome process, when every record has to be fetched from an underlying data store and plotted as a graph of parallel co-ordinates. Also, a graph of a large group of records may become indecipherable due to a crowded plot of lines, thereby defeating the purpose of parallel co-ordinates.

BRIEF DESCRIPTION OF THE DRAWINGS

The claims set forth the embodiments with particularity. The embodiments are illustrated by way of examples and not by way of limitation in the figures of the accompanying drawings in which like references indicate similar elements. The embodiments, together with its advantages, may be best understood from the following detailed description taken in conjunction with the accompanying drawings.

DETAILED DESCRIPTION

Embodiments of techniques to generate a visualization of parallel co-ordinates are described herein. A parallel co-ordinate is a method of visualizing and analyzing multivariate data. By analyzing the parallel co-ordinates, a flow of records of data and a relation between corresponding attributes can be inferred. To analyze the parallel co-ordinates, the graph of parallel co-ordinates is segmented. The underlying records are grouped into separate buckets. An aggregation of the bucketed records is determined from an associated database, and plotted on a graph to generate the visualization of the parallel co-ordinates.

In the following description, numerous specific details are set forth to provide a thorough understanding of the embodiments. One skilled in the relevant art will recognize, however, that the embodiments can be practiced without one or more of the specific details, or with other methods, components, materials, etc. In other instances, well-known structures, materials, or operations are not shown or described in detail.

Reference throughout this specification to "one embodiment", "this embodiment" and similar phrases, means that a particular feature, structure, or characteristic described in connection with the embodiment is included in at least one of the one or more embodiments. Thus, the appearances of these phrases in various places throughout this specification are not necessarily all referring to the same embodiment. Furthermore, the particular features, structures, or characteristics may be combined in any suitable manner in one or more embodiments.

Figure 1:
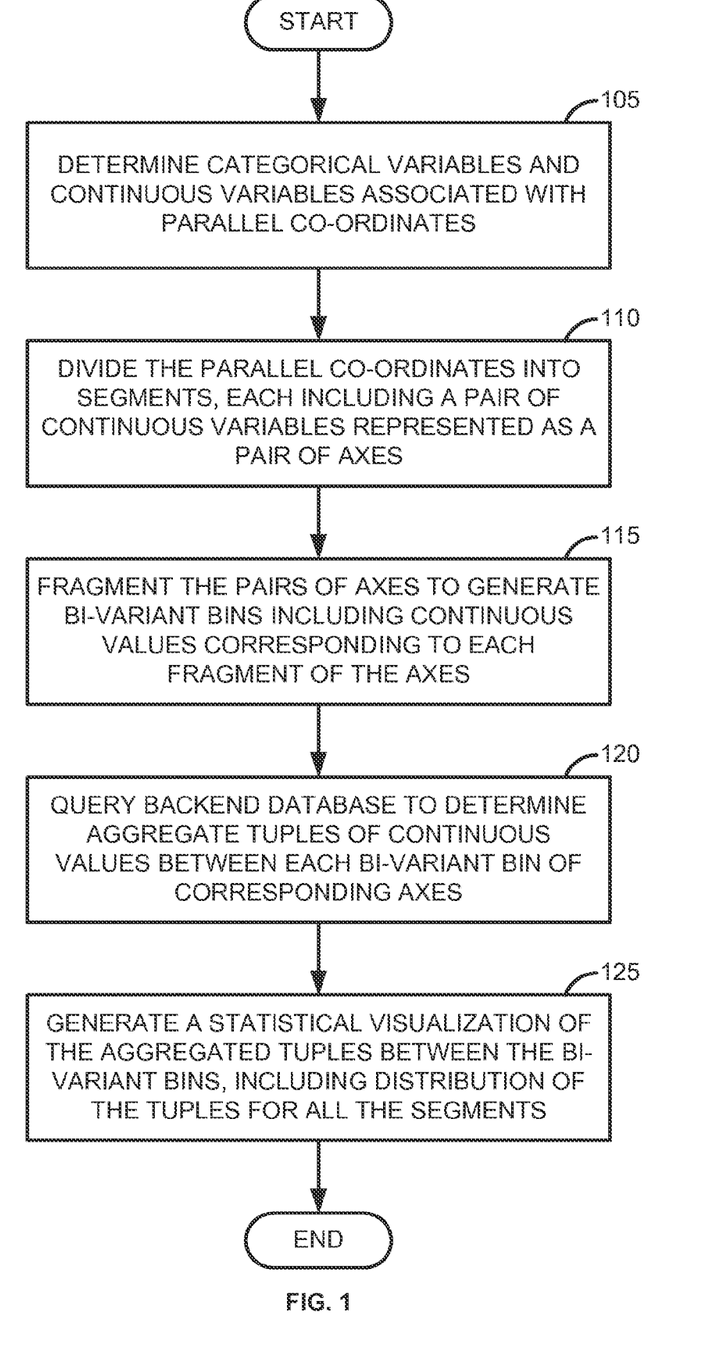
FIG. 1 is a block diagram illustrating a process flow of a method to generate a visualization of parallel co-ordinates, according to an embodiment.

FIG. 1 is a block diagram illustrating a process flow of a method to generate a visualization of parallel co-ordinates, according to an embodiment. Parallel co-ordinates associated with a business scenario represent underlying multivariate data of the business scenario. The multivariate data of the business scenario may include multiple records of data, representing multiple values and corresponding fields, which may be residing in a database table. Such records are also referred to as tuples. The parallel co-ordinates of the business scenario include a plurality of polylines, a plurality of axes, and a plurality of vertices on the axes. In an embodiment, the polylines represent a series of connected line segments, where each line segment is a plot of underlying tuple; the axes represent data set associated with data elements; and the vertices on the axes represent coordinates of an element under analysis.

A process flow illustrated in FIG. 1 explains a method to generate a visualization of the parallel co-ordinates, according to an embodiment. In process block 105, categorical variables and continuous variables associated with the parallel co-ordinates are determined. A categorical variable associated with the parallel co-ordinates represents a plurality of possible categorical data associated with the parallel co-ordinates. For example, a blood type of a person can categorically be 'A', 'B' 'AB' or 'O'. In another example, for a business scenario of analyzing 'Iris flower data set', the possible categorical variables include three plant species of *Iris*, namely '*Iris Setosa*', '*Iris Virginica*', and '*Iris Versicolor*'. An entry in the database table illustrating such categorical data may be referred to as categorical variable. In an embodiment, the blood types 'A', 'B', 'AB', 'O' and *Iris* plant species '*Iris Setosa*', '*Iris Virginica*', and '*Iris Versicolor*' are referred to as categorical values. A continuous variable associated with the parallel co-ordinates represent a plurality of attributes of the corresponding continuous variable. For instance, for a plant species '*Iris Setosa*', petal width, petal length, sepal width, and sepal length represent the attributes of the categorical variable '*Iris Setosa*'.

In process block 110, the parallel co-ordinates are divided into a plurality of segments. Each such segment includes a pair of continuous variables represented as a pair of axes. The parallel co-ordinates may be divided at each axis such that each segment includes the polylines plotted between the pair of axes. Each segment represents a data flow between the pair of axes corresponding to that segment. The continuous variables represented as a pair of axes, illustrate database fields, for instance, dimensions, associated with the parallel co-ordinates. For example, a sepal length, a sepal width, a petal length, a petal width, and the like corresponding to the species 'Iris Setosa', 'Iris Virginica', and 'Iris Versicolor'.

In process block 115, the pairs of axes of each segment are fragmented to generate bi-variant bins. A bi-variant bin includes a pair of bins representing two degrees of variations—a first degree associated with a first axis and a second degree associated with a second axis of a segment. Between every bi-variant bin, there may be zero or more polylines representing a plot of zero or more continuous values between the two corresponding axes. The bi-variant bins include continuous values associated with each fragment of the axes. Here, a first axis of the pair of axes is fragmented into a finite number of bins, where each bin represents the attributing continuous value associated with the continuous variable corresponding to the first axis. A second axis of the pair of axes is fragmented into a finite number of bins, where each bin represents the attributing continuous value associated with the continuous variable corresponding to the second axis. The bi-variant bins are generated by consolidating the bins from the first axis and the bins from the second axis. The continuous values associated with the fragment represent numeric data, for instance a measure, associated with the categorical variables and the continuous variables. For example, if a sepal length of Iris Setosa is 5.4 millimeter, the attributing continuous value is '5.4'. In an embodiment, the number of bins is determined based upon a user defined value, a machine defined value, a screen size of an associated user interface, a number of associated continuous values, and the like.

In process block 120, a backend database associated with the parallel co-ordinates is queried to determine aggregate tuples of continuous values between each bi-variant bin of corresponding axes. The backend database may include a database table representing the tuples as categorical variables, categorical values, the continuous variables and the corresponding continuous values in a tabular manner. The database table may also include a count of continuous values of corresponding tuples, an aggregation of continuous values of corresponding tuples, and the like, represented as aggregated tuples. Based on the aggregated tuples, a count of tuples corresponding to each bi-variant bin is determined by aggregating the corresponding number of continuous values. Similarly, based on the aggregated tuples, an aggregation of continuous values corresponding to each bi-variant bin is determined by aggregating the corresponding continuous values. The count of continuous values and the aggregation of continuous values are stored as aggregated tuples in the database table. In process block 125, a visualization of the aggregated tuples between the bi-variant bins is generated. This visualization includes a distribution of the tuples for all the segments. By analyzing the visualization of the parallel co-ordinates, a flow of the tuples and a relation between the categorical variables and the continuous variables can be inferred.

Figure 2:
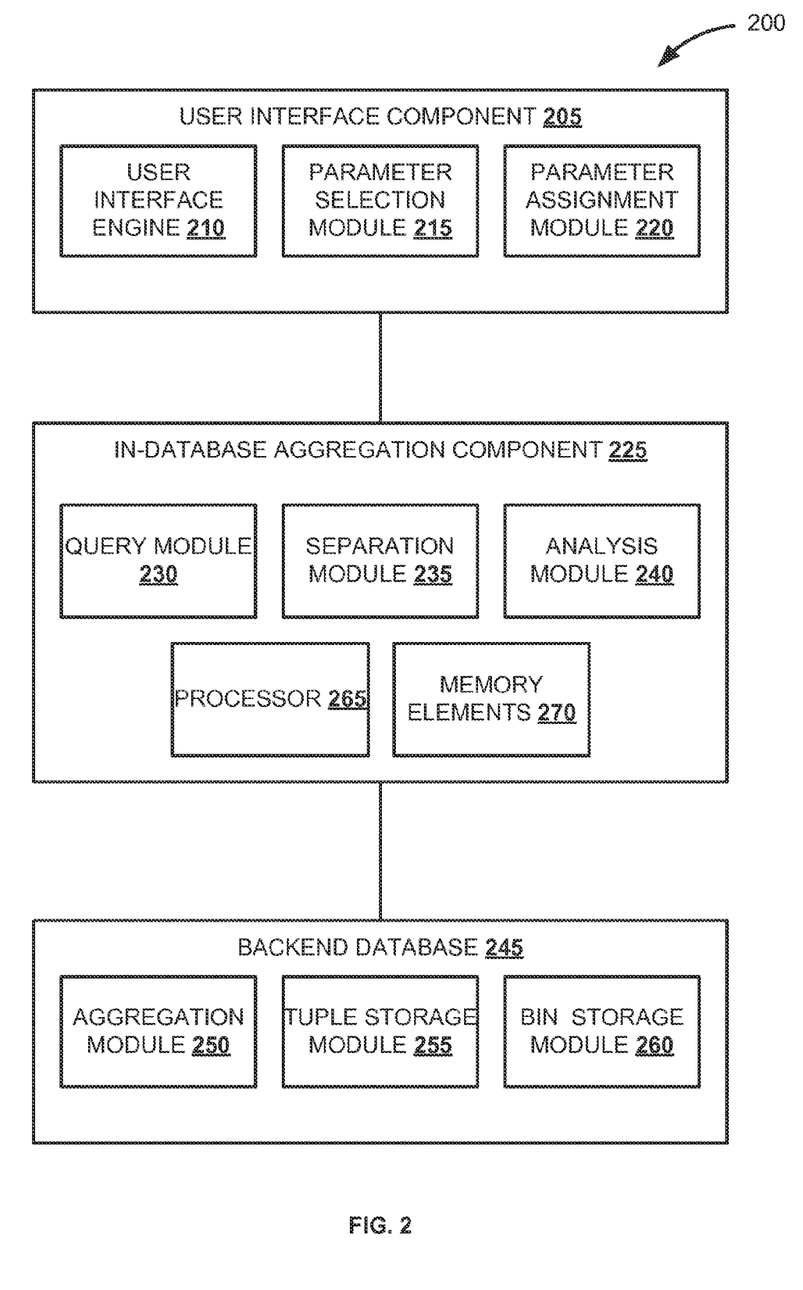
FIG. 2 is a block diagram illustrating a system to generate a visualization of parallel co-ordinates, according to an embodiment.

FIG. 2 is a block diagram illustrating a system to generate a visualization of parallel co-ordinates, according to an embodiment. System 200 is an exemplary system to generate a visualization of parallel co-ordinates. System 200 includes user interface component 205 comprising user interface engine 210, parameter selection module 215 and parameter assignment module 220; in-database aggregation component 225 comprising query module 230, separation module 235 and analysis module 240; and backend database 245 comprising aggregation module 250, tuple storage module 255 and bin storage module 260. In an embodiment, processor 265 is configured to read and execute instructions stored in memory elements 270; and memory elements 270 store instructions to generating a visualization of parallel co-ordinates.

In an embodiment, a selection of a business scenario is received on a user interface associated with user interface component 205, for generating a visualization of parallel co-ordinates associated with the business scenario. The parallel co-ordinates include axes, polylines and vertices on the axes as parameters of the parallel co-ordinates. User interface engine 210 triggers an in-database aggregation process to generate the visualization. In response to the trigger, processor 265 determines the categorical variables and the continuous variables corresponding to the parallel co-ordinates associated with the business process from tuple storage module 255. In an embodiment, a user elects one or more of a plurality of categorical variables for analysis. For instance, if the business scenario 'Iris flower data set' includes three categorical variables: 'Iris plant type, 'Iris plant color', and 'Iris plant fragrance', a user can select 'Iris plant type' as a categorical value for analysis. For a backend database determination, a data type associated with the categorical variables may be used to distinguish categorical variables and continuous variables. For example, the categorical variables 'Iris plant type', 'Iris plant color', and 'Iris plant fragrance' are of string type; whereas, the continuous variables may be of integer type. In an embodiment, processor 265 assigns the categorical values of the (elected) categorical variable to a group of polylines of the parallel co-ordinates; assigns the continuous variables to the axes of the parallel co-ordinates; and assigns the continuous values to the vertices intersecting the axes of the parallel co-ordinates.

Parameter selection module 215 is initiated to select a categorical value for analysis. Based upon the categorical values selected, processor 265 triggers separation module 235 to divide the parallel co-ordinates to perform analysis. Separation module 235 divides the parallel co-ordinates into a plurality of segments at the axes of the parallel co-ordinates, by determining a position to divide the parallel co-ordinates. In an embodiment, the parallel co-ordinates are divided at every axes representing corresponding continuous variables. Thus, each divided segment includes a pair of continuous variables represented as a pair of axes of the parallel co-ordinates. The pair of axes marks the bounds for the corresponding segment, and represents the dataflow of tuples between the corresponding two axes. Metadata associated with the dividing of the parallel co-ordinates, for instance, a position of dividing, a continuous variable of the segment, and the like, are stored in tuple storage module 255.

Separation module 235 fragments the pairs of axes corresponding to the segments to generate bi-variant bins including continuous values corresponding to each fragment. Fragmenting an axis includes determining a range of continuous values associated with the corresponding axis, and dividing the range of continuous values into a finite number of bins. For instance, if a sepal width of Iris Setosa varies between 3.5 mm and 1.4 mm, the range of continuous values is represented as 3.5-1.4. This range may be divided into thirty bins, and the continuous values are plotted on to the thirty bins. Each bin includes zero or more continuous values having vertices present in the corresponding bin. For instance, a fourth bin includes the sepal width 3.5 mm since the vertex representing 3.5 mm is included in a fourth fragment of the corresponding axis.

In an embodiment, separation module 235 fragments a first axis of a segment into a first set of finite bins, where each bin represents the attributing continuous values associated with a continuous variable corresponding to the first axis. Similarly, separation module 235 fragments a second axis of a segment into a second set of finite bins, where each bin represents the attributing continuous values associated with a continuous variable corresponding to the second axis. The separation module consolidates the bins from the first axis and the second axis to generate the bi-variant bins. This procedure is repeated for all the segments of the parallel co-ordinates. Metadata associated with the fragmentation of the parallel co-ordinates, for instance, a position of vertex in each fragment, a continuous variable of the bin, a number of vertices present in a bin, and the like, are stored in bin storage module 260.

Query module 230 queries backend database 245 to determine aggregated tuples of continuous values between each bi-variant bin of the corresponding pair of axes. Backend database 245 may include a database table representing the tuples as categorical variables, the continuous variables and the corresponding continuous values in a tabular manner. Aggregated tuples and aggregation information of the tuples are determined and stored in the database table residing in aggregation module 250. In an embodiment, the aggregated tuples are determined by aggregation module 250, based upon a trigger to execute an in-database aggregation.

Analysis module 240 generates a statistical visualization of the aggregated tuples between the bi-variant bins for the axes associated with the parallel co-ordinates on the computer generated user interface associated to the user interface engine 210. Generating a statistical visualization includes generating a distribution of the tuples for each segment to represent a dataflow between the pairs of axes corresponding to the segment and generating the distribution of tuples for the plurality of segments to represent a dataflow for all the segments. Generating a statistical visualization also includes implementing a bi-variant plotting of the tuples for the plurality of segments corresponding to the parallel co-ordinates. A bi-variant plotting of tuples includes determining continuous values between each bi-variant bin for each segment of the parallel co-ordinate and plotting the determined continuous values.

In an embodiment, a density of the aggregated tuples is determined, and a degree of density of the aggregated tuples is plotted for each bi-variant bin. A density of the aggregated tuples represents a quantity of tuples for every bi-variant bin. For instance, if a first bi-variant bin is associated with seven tuples, and a third bi-variant bin is associated with fourteen tuples, the aggregated tuples for the first bi-variant bin is said to be dense compared to the aggregated tuples for the second bi-variant bin. A degree of density illustrating a statistical analysis of the density of the tuples is plotted on the parallel co-ordinates. The degree of density denotes a density of flow of tuples from one continuous variable to another, a relation between two or more continuous variables, a distribution of density of tuples for the categorical variables, a distribution of density of tuples across all continuous variables, and the like. In an embodiment, the degree of density is plotted using various visual representations including line patterns, line colors, n-dimensional patterns, shapes, symbols and the like. For example, varied thickness of lines can represent varied degrees of density of the tuples. Plotting such lines with varied thickness across the parallel co-ordinates, or providing any similar statistical visualization of the parallel co-ordinates provides a comprehension of the flow of tuples of data across the parallel co-ordinates and a relation between corresponding continuous variables.

In an embodiment, separation module 235 triggers parameter assignment module 220 to assign parameters to the parallel co-ordinates. The parameters include categorical variables and categorical values associated with pairs of axes of the segments, categorical values associated with bi-variant bins of the segments, aggregated tuples, and the like.

In an embodiment, the segments are categorized based upon the categorical values associated with the parallel co-ordinates, to select individual categories of segments for fragmenting the corresponding pairs of axes. For example, the species '*Iris Setosa*', '*Iris Virginica*', and '*Iris Versicolor*' may include three corresponding individual groups of polylines in the parallel co-ordinates representing the plot of continuous values associated with the respective species. Here, the groups of polylines in the segments may be represented distinctively from each other, for instance using three distinctive colors for the three categories, using three patterns of lines for the three categories, or the like. The fragmentation of segments, determination of the aggregated tuples and the generation of the statistical visualization may be executed separately for the three categories. Further, the categorical statistical visualization for the three species may be merged to generate a consolidated statistical visualization for the entire parallel co-ordinates for the received business process.

In an embodiment, the tuples associated with the parallel co-ordinates are grouped into separate database buckets at backend database 245. The in-database aggregation component 225 may generate the database buckets, and associate the buckets with the bi-variant bins. An aggregation of the bucketed tuples is determined by aggregation module 250, and plotted on a graph to generate the visualization of the parallel co-ordinates. A process of executing the aggregations at an in-database level to determine the aggregated tuples may be referred to as in-database aggregation mechanism.

Figure 3:
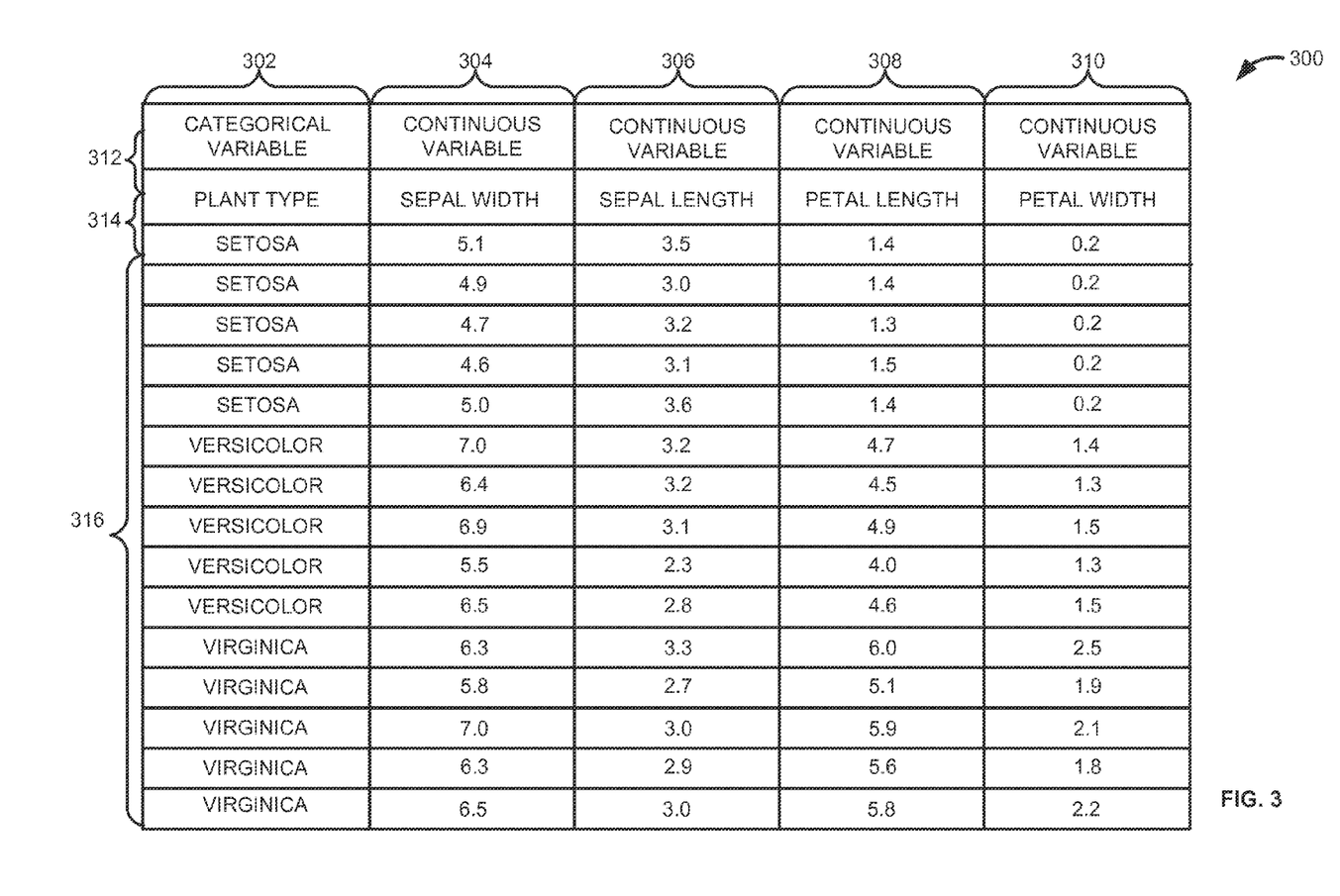
FIG. 3 is a block diagram illustrating an exemplary backend database table involved in a method to generate a visualization of parallel co-ordinates, according to an embodiment.

FIG. 3 is a block diagram illustrating an exemplary backend database table involved in a method to generate a visualization of parallel co-ordinates, according to an embodiment. Backend database table 300 includes tuples arranged as categorical variable(s) represented in column 302, continuous variables represented in columns 304, 306, 308 and 310 and the corresponding continuous values represented in rows 316. Row 312 denotes the categorical variables and the continuous variables from their respective columns. Row 314 denotes exemplary entries for the categorical variables and continuous variables in row 312. The database table may also include a count of continuous values of corresponding tuples, an aggregation of continuous values of corresponding tuples, and the like, represented as aggregated tuples. In an embodiment, database table 300 is employed to perform in-database aggregation and determine the aggregated tuples, at in-database level. Table 300 includes a partial group of categorical variables, continuous variables and continuous values of an "*Iris* flower data set". It is to be noted that the *Iris* flower data set is an example considered to provide a thorough understanding of the embodiments only, and the embodiments are not limited by the illustration. Categorical variables in 302 include three plant types, namely, '*Setosa*', '*Versicolor*' and '*Virginica*'. Continuous variables in 304, 306, 308 and 310 include 'Sepal width', 'Sepal length', 'Petal width' and 'Petal length' of the three plants. The numeric values in rows illustrated by element 316 for columns 304, 306, 308 and 310 represent the measurements of the continuous variables for a group of plants of the three plant types. A plot of the partial group of tuples is illustrated in FIG. 4.

Figure 4:
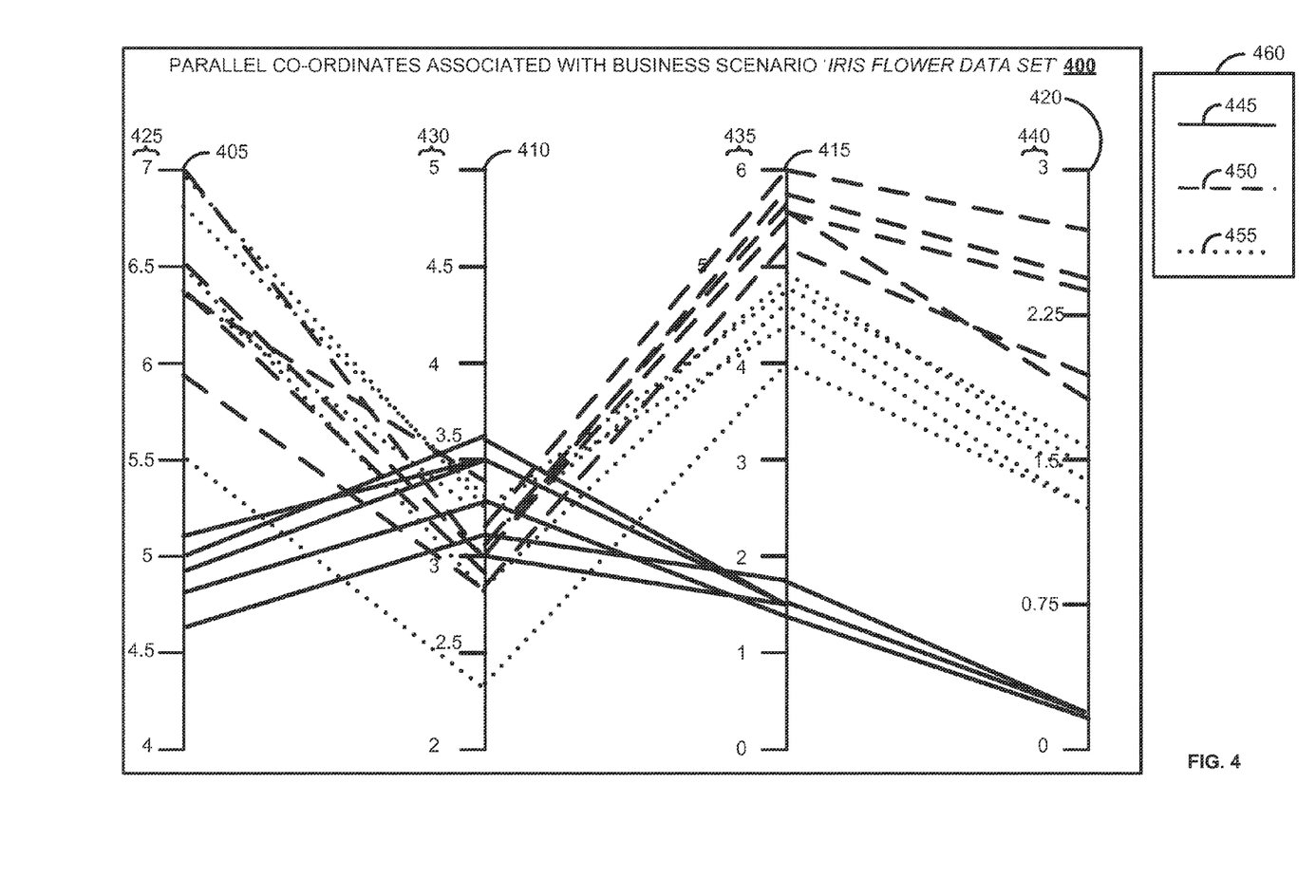
FIG. 4 is an illustration of parallel co-ordinates involved in a method to generate a visualization of parallel co-ordinates, according to an embodiment.

FIG. 4 is an illustration of parallel co-ordinates involved in a method to generate a visualization of parallel co-ordinates, according to an embodiment. For the tuples arranged in database table 300, plot 400 of parallel co-ordinates includes axis 405 representing categorical variable of column 304 (in FIG. 3), axis 410 represents continuous variable of column 306 (in FIG. 3), axis 415 represents continuous variable of column 308 (in FIG. 3), and axis 420 represents continuous variable of column 310 (in FIG. 3). Elements 425, 430, 435 and 440 represent continuous values associated with continuous variables 415, 420, 425 and 430 respectively. Legend 460 illustrates three categorical values including three types of lines used to represent three species of plants in the "*Iris* flower data set", where, 'solid line' 445 represents a plot of tuples for *Setosa*, 'dotted line' 455 represents a plot of tuples for *Versicolor*, and 'dashed line' 450 represents a plot of tuples for *Virginica*.

Figure 5:
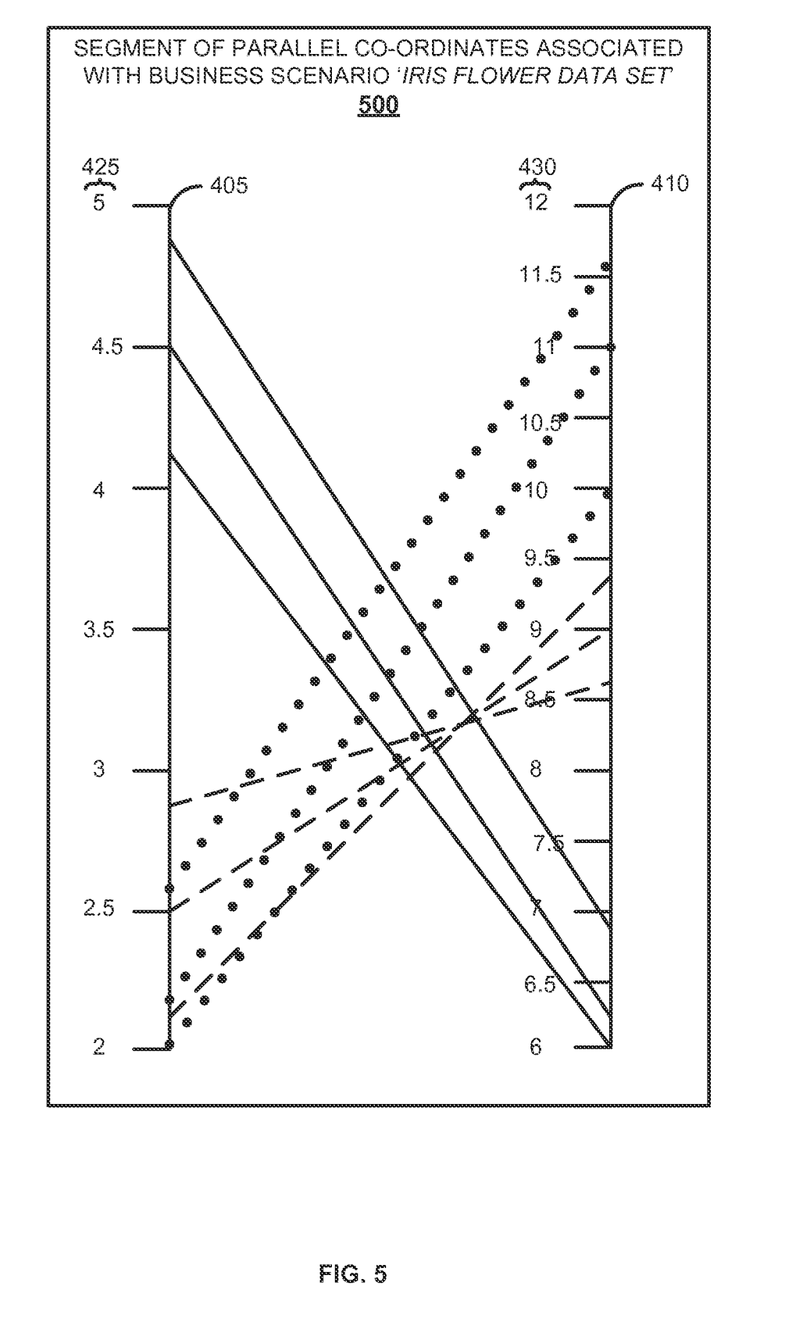
FIG. 5 is an illustration of a segment of parallel co-ordinates involved in a method to generate a visualization of parallel co-ordinates, according to an embodiment.

FIG. 5 is an illustration of a segment of parallel co-ordinates involved in a method to generate a visualization of parallel co-ordinates, according to an embodiment. In an embodiment, segment 500 is an outcome of dividing the plot 400 based upon the associated categorical values. Segment 500 includes a pair of axes—representing a pair of continuous variables 405 and 410. The continuous variables 405 and 410 mark the bounds for segment 500, and represents dataflow between the continuous variables 405 and 410. For instance, the continuous values (polylines) of the three species of plants between the continuous variables 405 and 410 represent the dataflow between the corresponding continuous variables (405 and 410). Segment 500 represents a first segment of three segments associated with the parallel co-ordinate represented in plot 400 (in FIG. 4). A second segment of the three segments may include continuous variables 410 and 415 and the plot of the corresponding continuous values. Similarly, a third segment may include continuous variables 415 and 420 and the plot of the corresponding continuous values.

Figure 6A:
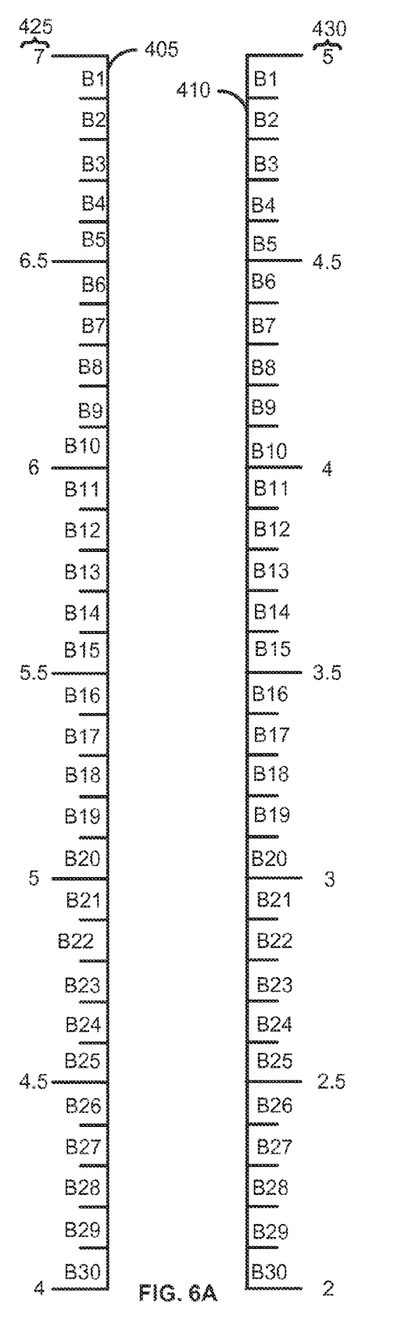
FIG. 6A is an illustration of axes involved in a method to generate a visualization of parallel co-ordinates, according to an embodiment.

FIG. 6A is an illustration of axes involved in a method to generate a visualization of parallel co-ordinates, according to an embodiment. The pairs of continuous variables 405 and 410 represented as the pairs of axes of the segment 500 are fragmented to generate 'bi-variant bins B1-B30' of 405 and 'bi-variant bins B1-B30' of 410, including continuous values '4, 5, 6, 7' of 405 and '2, 3, 4, 5' of 410 corresponding to each fragment. The bi-variant bins include a pair of bins, for example B1 of 405 and B1 of 410, representing two degrees of variation, where a first degree of variation 'B1 of 405' is associated with the first axis 405 and a second degree of variation 'B1 of 410' is associated with the second axis 410. Thus the two degrees 'B1 of 405' and 'B1 of 410' together constitute a bi-variant bin. Between every bi-variant bin, there may be zero or more polylines representing a corresponding plot of zero or more continuous values. Bi-variant bins include all combinations of a first degree of variation from 405 and a second degree of variation from 410. For instance, B1 of 405 and B2 of 410; B1 of 405 and B3 of 410; B1 of 405 and B4 of 410; and the like.

Figure 6B:
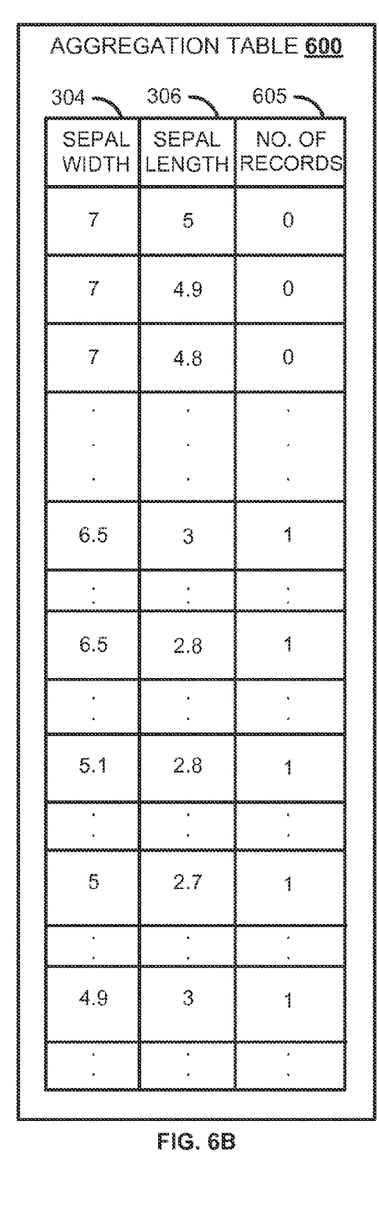
FIG. 6B is a block diagram illustrating a backend table involved in a method to generate a visualization of parallel co-ordinates, according to an embodiment.

FIG. 6B is a block diagram illustrating a backend table involved in a method to generate a visualization of parallel co-ordinates, according to an embodiment. Aggregation table 600, associated with database table 300, includes a count of continuous values of corresponding tuples, an aggregation of continuous values of corresponding tuples, and the like, represented as aggregated tuples. Based on the aggregated tuples, a count of tuples corresponding to each bi-variant bin is determined by aggregating the corresponding number of continuous values. Similarly, based on the aggregated tuples, an aggregation of continuous values corresponding to each bi-variant bin is determined by aggregating the corresponding continuous values. The count of continuous values and the aggregation of continuous values are stored as aggregated tuples in aggregation table 600.

Aggregation table 600 includes the continuous variables for all the segments associated with the parallel co-ordinates. For instance, aggregation table 600 includes continuous variables "sepal width" 304 and "sepal length" 306 associated with first segment 500, along with corresponding continuous values. Aggregation table 600 also includes the count and aggregation information required to generate aggregated tuples. For instance, aggregation table 600 includes "number of tuples" column 605. When a backend database is queried, the aggregated tuples of continuous values between each bi-variant bin of the corresponding continuous variables is determined. In aggregation table 600, the continuous values for the continuous variables 304 and 306 are included as no of records in the rows of column 605. For example, the aggregated tuples between continuous value 7 of continuous variable 405 and continuous value 5 of continuous variable 410 is zero (no tuples). The aggregated tuples between continuous value 6.5 of continuous variable 405 and continuous value 3 of continuous variable 410 is one (one tuple).

In an embodiment, the aggregated tuples are determined based upon a trigger to execute an in-database aggregation. The in-database aggregation is executed at an in-database level, by determining a count of continuous values of corresponding tuples, an aggregation of continuous values of corresponding tuples, and the like, represented as aggregated tuples. Based on the aggregated tuples, a count of tuples corresponding to each bi-variant bin is determined by aggregating the corresponding number of continuous values. Similarly, based on the aggregated tuples, an aggregation of continuous values corresponding to each bi-variant bin is determined by aggregating the corresponding continuous values.

Figure 7:
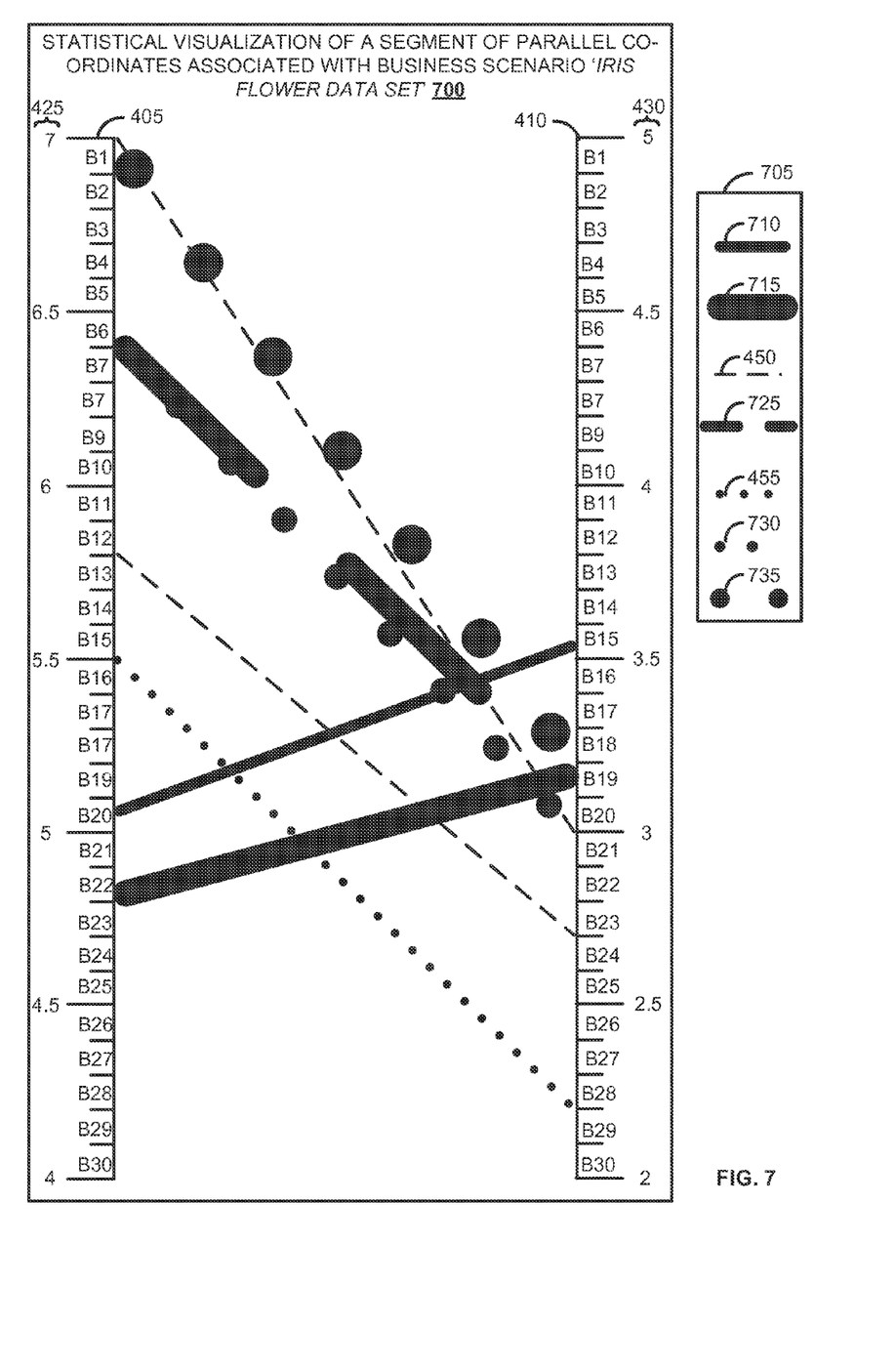
FIG. 7 is an illustration of axes involved in a method to generate a visualization of parallel co-ordinates, according to an embodiment.

FIG. 7 is an illustration of axes involved in a method to generate a visualization of parallel co-ordinates, according to an embodiment. FIG. 7 represents a statistical visualization 700 of the aggregated tuples between the bi-variant bins associated with axes 405 and 410 of first segment 500. Dataflow between the continuous variables 405 and 410 is plotted by connecting the corresponding vertices associated with the continuous values with polylines. Segment 700 represents an implementation of bi-variant plotting of the tuples for each segment.

Legend 705 includes three categorical values illustrated by three types of lines used to represent three species of plants in the "*Iris* flower data set", where, 'solid line' 445 represents a plot of tuples for *Setosa*, 'dotted line' 455 represents a plot of tuples for *Versicolor*, and 'dashed line' 450 represents a plot of tuples for *Virginica*. Legend 705 also illustrates various densities of the lines included in segment 700. In segment 700, the thickness of lines connecting the corresponding continuous values represents the density of the aggregated tuples for the corresponding bi-variant bins. Solid lines 710 and 715 represent three densities of tuples for *Setosa*; dotted lines 455, 730 and 735 represent two densities of tuples *Versicolor*; and dashed lines 450 and 725 represent two densities of tuples for *Virginica*.

For instance, the thickness of the solid line 710 representing the plot for tuples of *Setosa* between bi-variant bins B20 of 405 and B15 of 410 depicts a density of two tuples; the thickness of the solid line 715 between bi-variant bins B22-B23 of 405 and B19 of 410 depicts a density of three tuples. Hence, the thickness of the polylines representing the two tuples is less dense compared to the thickness of the polylines representing the three tuples.

The dotted lines representing the plot of tuples for *Versicolor* has three variations of density. The plot between B1-B2 of 405 and B18-B19 of 410 has a high density since the polylines connecting two corresponding continuous values are overlapping with each other. The plot between B5-B7 of

405 and B19-B22 of 410 has a medium density since the polylines connecting two continuous values are adjacent to each other. The plot between B15 of 405 and B28 of 410 has a low density since the polyline connecting one continuous value is isolated from the rest of the plots.

The dashed lines representing the plot of tuples for *Virginica* has three variations of density. The plot between B6-B7 of 405 and B19-B20 of 410 has a high density since there are three polylines, and the polylines connecting the corresponding continuous values are overlapping with each other. The plot between B12-B13 of 405 and B23-B24 of 410 have a low density since there is only one polyline each, connecting the continuous values.

In an embodiment, the density of the tuples is associated with the range of bi-variant bins. For instance, if the range of the bi-variant bins is short, and the number of polylines is more, the plot of such polylines will have a high density compared to a plot of bi-variant bins with a large range and more number of poly lines. For example, if there are ten polylines between B19-B23 of first axes and B5-B7 of second axis; and there are nine polylines between B17 of first axis and B25-26 of second axis, the thickness of the polylines with the second group is dense compared to the thickness of the polylines of the first group. The reason for this analysis may be associated with the proximity of the continuous values of the continuous variables. For example, in the first group, the values of the bi-variant bins may vary between 5.6-5.9 millimeters and 2.8-3.1 millimeters; and in the second group the values of the bi-variant bins may vary between 5.6-5.7 millimeters and 2.1-2.3 millimeters. Since the proximity of continuous values is high in the second group, the polylines present in the second group are dense compared to the polylines present in the first group.

Figure 8:
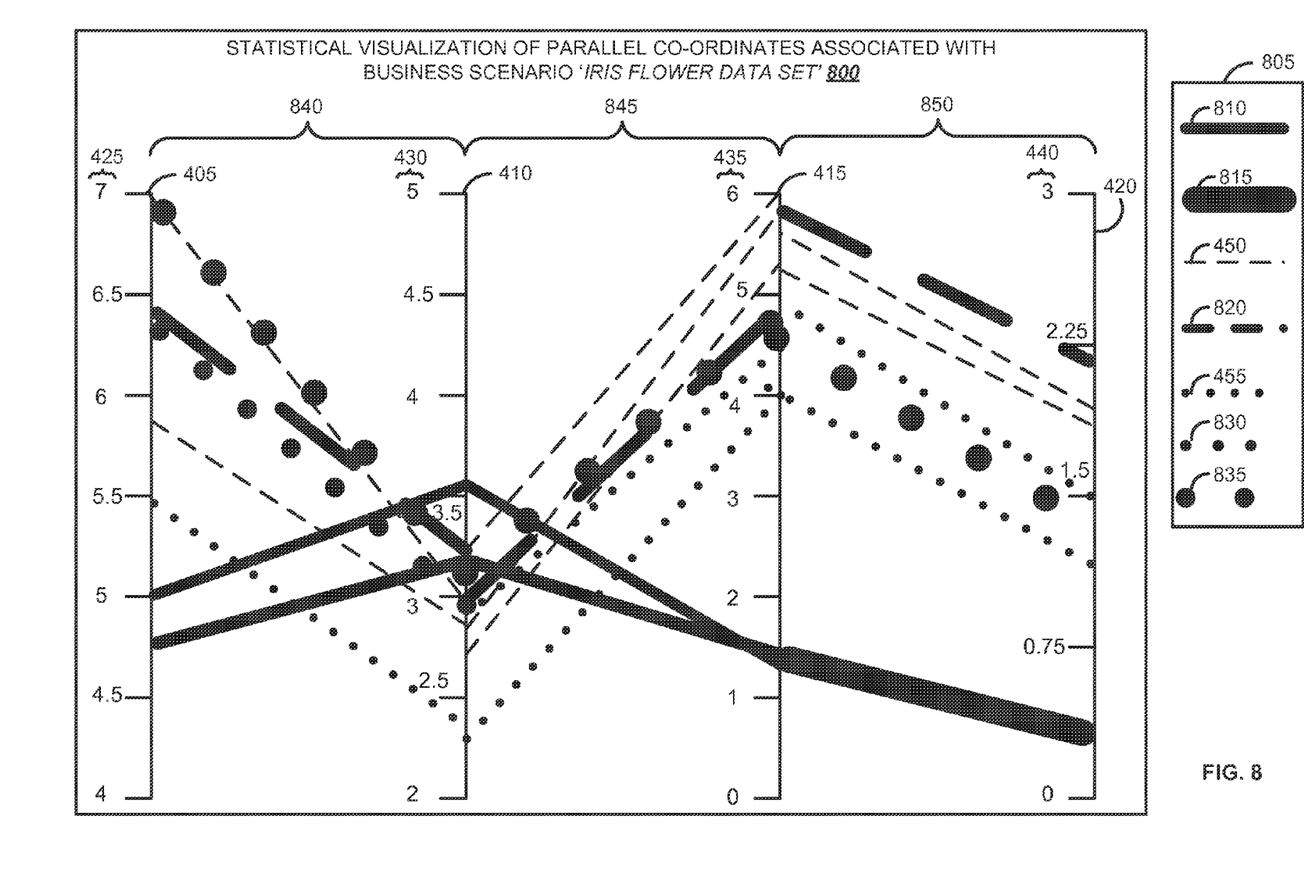
FIG. 8 is an illustration of a visualization of parallel co-ordinates, according to an embodiment.

FIG. 8 is an illustration of a visualization of parallel co-ordinates, according to an embodiment. In a manner similar to the description of FIG. 7, all the segments 840, 845 and 850 of the parallel co-ordinates are plotted to generate the statistical visualization of the aggregated tuples between the bi-variant bins for the axes. Legend 805 illustrates the polylines of the continuous values along with various densities. For instance, 810, and 815 depict two densities of the tuples associated with *Setosa*; 450, and 820 depict two densities of the tuples associated with *Virginica*; and 455, 830 and 835 depict three densities of the tuples associated with *Versicolor*. By analyzing the parallel co-ordinates 800, a flow of tuples of each categorical value '*Setosa*', '*Versicolor*' and '*Virginica*', along the continuous variables and corresponding continuous values is determined. In addition, a relation of the categorical values with each continuous variable can be inferred. For example, by analyzing the statistical visualization of the parallel co-ordinates 800, it can be observed that a high sepal width 405 of *Versicolor* (455, 830, 835) and *Virginica* (450, 820), corresponds to a low the sepal length 410; and a low sepal width 405 of *Setosa* (810, 815).

Some embodiments may include the above-described methods being written as one or more software components. These components, and the functionality associated with each, may be used by client, server, distributed, or peer computer systems. These components may be written in a computer language corresponding to one or more programming languages such as, functional, declarative, procedural, object-oriented, lower level languages and the like. They may be linked to other components via various application programming interfaces and then compiled into one complete application for a server or a client. Alternatively, the components maybe implemented in server and client applications. Further, these components may be linked together via various distributed programming protocols. Some example embodiments may include remote procedure calls being used to implement one or more of these components across a distributed programming environment. For example, a logic level may reside on a first computer system that is remotely located from a second computer system containing an interface level (e.g., a graphical user interface). These first and second computer systems can be configured in a server-client, peer-to-peer, or some other configuration. The clients can vary in complexity from mobile and handheld devices, to thin clients and on to thick clients or even other servers.

The above-illustrated software components are tangibly stored on a computer readable storage medium as instructions. The term "computer readable storage medium" should be taken to include a single medium or multiple media that stores one or more sets of instructions. The term "computer readable storage medium" should be taken to include any physical article that is capable of undergoing a set of physical changes to physically store, encode, or otherwise carry a set of instructions for execution by a computer system which causes the computer system to perform any of the methods or process steps described, represented, or illustrated herein. A computer readable storage medium may be a non-transitory computer readable storage medium. Examples of a non-transitory computer readable storage media include, but are not limited to: magnetic media, such as hard disks, floppy disks, and magnetic tape; optical media such as CD-ROMs, DVDs and holographic devices; magneto-optical media; and hardware devices that are specially configured to store and execute, such as application-specific integrated circuits ("ASICs"), programmable logic devices ("PLDs") and ROM and RAM devices. Examples of computer readable instructions include machine code, such as produced by a compiler, and files containing higher-level code that are executed by a computer using an interpreter. For example, an embodiment may be implemented using Java, C++, or other object-oriented programming language and development tools. Another embodiment may be implemented in hard-wired circuitry in place of, or in combination with machine readable software instructions.

Figure 9:
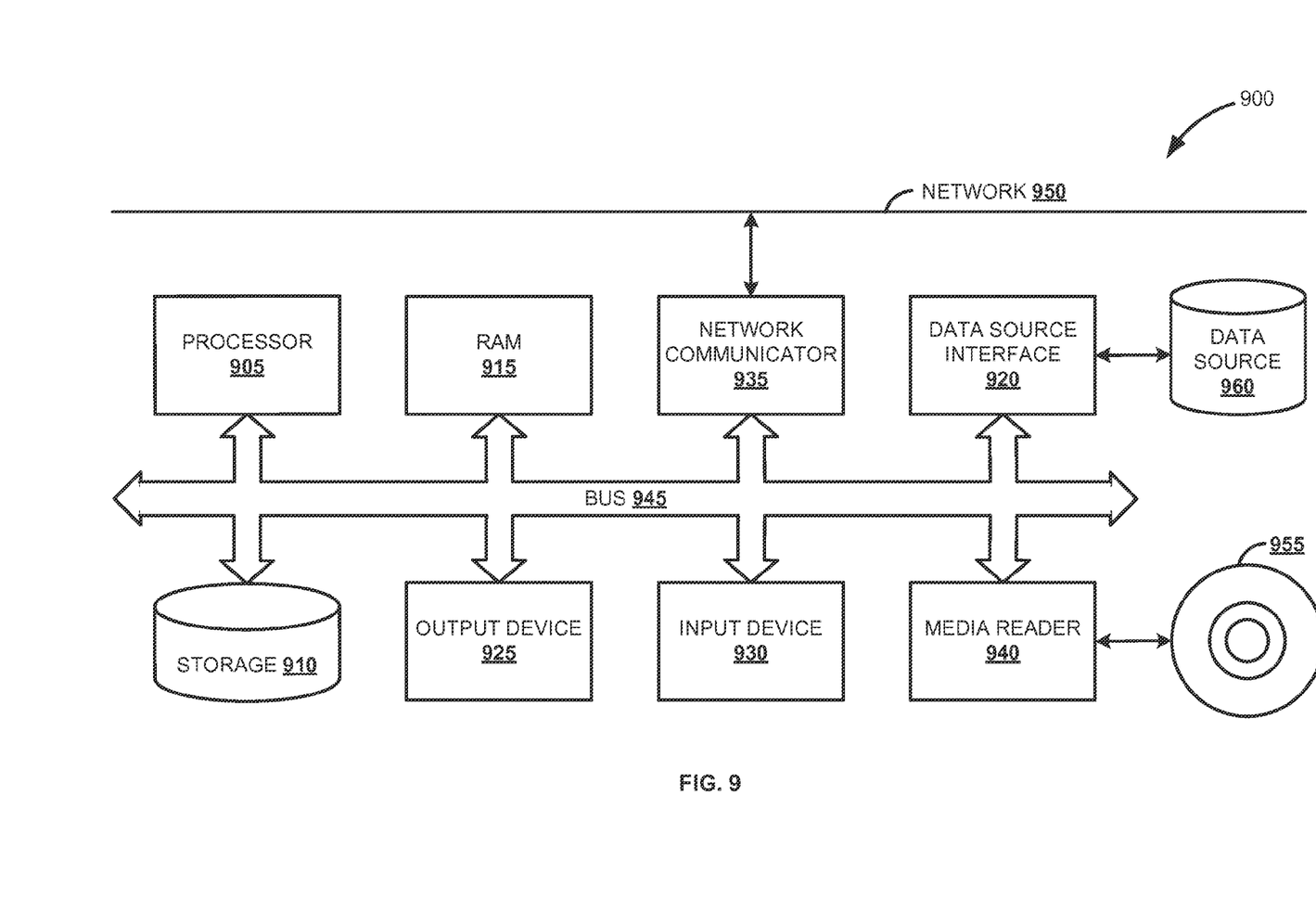
FIG. 9 is a block diagram illustrating an exemplary computer system, according to an embodiment.

FIG. 9 is a block diagram of an exemplary computer system 900. The computer system 900 includes a processor 905 that executes software instructions or code stored on a computer readable storage medium 955 to perform the above-illustrated methods. The processor 905 can include a plurality of cores. The computer system 900 includes a media reader 940 to read the instructions from the computer readable storage medium 955 and store the instructions in storage 910 or in random access memory (RAM) 915. The storage 910 provides a large space for keeping static data where at least some instructions could be stored for later execution. According to some embodiments, such as some in-memory computing system embodiments, the RAM 915 can have sufficient storage capacity to store much of the data required for processing in the RAM 915 instead of in the storage 910. In some embodiments, all of the data required for processing may be stored in the RAM 915. The stored instructions may be further compiled to generate other representations of the instructions and dynamically stored in the RAM 915. The processor 905 reads instructions from the RAM 915 and performs actions as instructed. According to one embodiment, the computer system 900 further includes an output device 925 (e.g., a display) to provide at least some of the results of the execution as output including, but not limited to, visual information to users and an input device 930 to provide a user or another device with means for entering data and/or otherwise interact with the computer system 900. Each of these output devices 925 and input devices 930 could be joined by one or more additional peripherals to further expand the capabilities of the computer system 900. A network communicator 935 may be provided to connect the computer system 900 to a network 950 and in turn to other devices connected to the network 950 including other clients, servers, data stores, and interfaces, for instance. The modules of the computer system 900 are interconnected via a bus 945. Computer system 900 includes a data source interface 920 to access data source 960. The data source 960 can be accessed via one or more abstraction layers implemented in hardware or software. For example, the data source 960 may be accessed by network 950. In some embodiments the data source 960 may be accessed via an abstraction layer, such as, a semantic layer.

A data source is an information resource. Data sources include sources of data that enable data storage and retrieval. Data sources may include databases, such as, relational, transactional, hierarchical, multi-dimensional (e.g., OLAP), object oriented databases, and the like. Further data sources include tabular data (e.g., spreadsheets, delimited text files), data tagged with a markup language (e.g., XML data), transactional data, unstructured data (e.g., text files, screen scrapings), hierarchical data (e.g., data in a file system, XML data), files, a plurality of reports, and any other data source accessible through an established protocol, such as, Open Data Base Connectivity (ODBC), produced by an underlying software system (e.g., ERP system), and the like. Data sources may also include a data source where the data is not tangibly stored or otherwise ephemeral such as data streams, broadcast data, and the like. These data sources can include associated data foundations, semantic layers, management systems, security systems and so on.

In the above description, numerous specific details are set forth to provide a thorough understanding of embodiments. One skilled in the relevant art will recognize, however that the embodiments can be practiced without one or more of the specific details or with other methods, components, techniques, etc. In other instances, well-known operations or structures are not shown or described in detail.

Although the processes illustrated and described herein include series of steps, it will be appreciated that the different embodiments are not limited by the illustrated ordering of steps, as some steps may occur in different orders, some concurrently with other steps apart from that shown and described herein. In addition, not all illustrated steps may be required to implement a methodology in accordance with the one or more embodiments. Moreover, it will be appreciated that the processes may be implemented in association with the apparatus and systems illustrated and described herein as well as in association with other systems not illustrated.

The above descriptions and illustrations of embodiments, including what is described in the Abstract, is not intended to be exhaustive or to limit the one or more embodiments to the precise forms disclosed. While specific embodiments and examples are described herein for illustrative purposes, various equivalent modifications are possible within the scope, as those skilled in the relevant art will recognize. These modifications can be made in light of the above detailed description. Rather, the scope is to be determined by the following claims, which are to be interpreted in accordance with established doctrines of claim construction.

What is claimed is:

1. A computer implemented method to generate a visualization of parallel coordinates, comprising:
    based upon one or more categorical variables associated with parallel co-ordinates of a business scenario, a processor of a computer dividing the parallel co-ordinates into a plurality of segments, each segment including a pair of continuous variables represented as a pair of axes of the parallel co-ordinates;
    fragmenting the pairs of axes to generate one or more bi-variant bins including one or more continuous values corresponding to each fragment of the pair of axes;
    querying a backend database associated with the parallel co-ordinates to determine one or more aggregated tuples of continuous values between the bi-variant bin of the corresponding pair of axes, the aggregated tuples are determined by:
        determining a count of tuples corresponding to each bi-variant bin by aggregating corresponding number of continuous values;
        determining an aggregation of continuous values corresponding to each bi-variant bin by aggregating the corresponding continuous values; and
        storing the count of continuous values and the aggregation of continuous values as
    aggregated tuples; and
    generating a statistical visualization of the aggregated tuples between the bi-variant bins for the axes associated with the parallel co-ordinates on a computer generated user interface, the statistical visualization including a distribution of the tuples for the plurality of segments corresponding to the parallel co-ordinates.

2. The computer implemented method of claim 1 further comprising:
    receiving a selection of the parallel co-ordinates representing multivariate data associated with a business scenario, the parallel co-ordinates including one or more polylines, the one or more axes, and one or more vertices on the axes;
    determining the categorical variables and the continuous variables associated with the multivariate data of the parallel co-ordinates, residing in the backend database;
    assigning the categorical variables to one or more groups of polylines of the parallel co-ordinates; and
    assigning the continuous variables to the axes of the parallel co-ordinates, and assigning the continuous values to the vertices of the axes of the parallel co-ordinates.

3. The computer implemented method of claim 1, wherein dividing the parallel coordinates include: dividing the parallel co-ordinates into the segments at each axis, wherein each segment represents a data flow between a pair of axes associated with the corresponding segment.

4. The computer implemented method of claim 1, wherein fragmenting the pair of axes comprises:
    fragmenting a first axis of the corresponding segment into a first set of finite bins, each bin representing the attributing continuous values associated with the continuous variable corresponding to the first axis;
    fragmenting a second axis of the corresponding segment into a second set of finite bins, each bin representing the attributing continuous values associated with the continuous variable corresponding to the second axis; and
    generating the bi-variant bins by consolidating the bins from the first axis and the bins from the second axis.

5. The computer implemented method of claim 4, wherein fragmenting further comprises:
    determining a range of the continuous values associated with the corresponding axis, and
    dividing the range of continuous values into a finite number of bins.

6. The computer implemented method of claim 1 further comprising: a backend database table representing the categorical variables, the continuous variables and the continuous values associated with the parallel co-ordinates.

7. The computer implemented method of claim 1 further comprising: generating one or more database buckets for the backend database table at an in-database aggregation level, wherein the database buckets correspond to the bi-variant bins.

8. The computer implemented method of claim 1 further comprising: in-database aggregation mechanism to determine the aggregated tuples.

9. The computer implemented method of claim 1 further comprising:
    categorizing the segments based upon the categorical variables, to select individual categories of the segments for fragmenting the corresponding pairs of axes; and
    consolidating the individual categories to generate the statistical visualization.

10. The computer implemented method of claim 1, wherein generating the statistical visualization comprises:
    generating a distribution of the tuples for each segment to represent a data flow between the pairs of axes corresponding to the segment;
    generating the distribution of tuples for the plurality of segments to represent a data flow for all the segments; and
    implementing bi-variant plotting of the tuples for the plurality of segments corresponding to the parallel co-ordinates.

11. The computer implemented method of claim 1 further comprising:
    determining a density of the aggregated tuples for each bi-variant bin; and
    plotting a degree of density of the aggregated tuples for each bi-variant bin in the statistical visualization.

12. The computer implemented method of claim 1, wherein the bi-variant bins represent two degrees of variation, comprising:
    a first degree associated with a first axis of a corresponding segment; and
    a second degree associated with a second axis of the corresponding segment.

13. An article of manufacture including a non-transitory computer readable storage medium to tangibly store instructions, which when executed by a computer, cause the computer to:
    divide parallel co-ordinates into a plurality of segments based upon one or more categorical variables associated with the parallel co-ordinates, each segment including a pair of continuous variables represented as a pair of axes of the parallel co-ordinates;
    fragment the pairs of axes to generate one or more bi-variant bins including one or more continuous values corresponding to each fragment of the axes;
    query a backend database associated with the parallel co-ordinates to determine one or more aggregated tuples of continuous values between the bi-variant bins of the corresponding pair of axes, the aggregated tuples are determined by:
        determining a count of tuples corresponding to each bi-variant bin by aggregating corresponding number of continuous values;
        determining an aggregation of continuous values corresponding to each bi-variant bin by aggregating the corresponding continuous values; and
        storing the count of continuous values and the aggregation of continuous values as aggregated tuples; and
    generate a statistical visualization of the aggregated tuples between the bi-variant bins for the axes associated with the parallel co-ordinates, the statistical visualization including a distribution of the tuples for the plurality of segments corresponding to the parallel co-ordinates.

14. The article of manufacture of claim 13 further including instructions to:
    receive a selection of the parallel co-ordinates representing multivariate data associated with a business scenario, the parallel co-ordinates including one or more polylines, the one or more axes, and one or more vertices on the axes;
    determine the categorical variables and the continuous variables associated with the multivariate data of the parallel co-ordinates, residing in the backend database;
    assign the categorical variables to one or more groups of polylines of the parallel co-ordinates; and
    assign the continuous variables to the axes of the parallel co-ordinates, and assigning the continuous values to the vertices of the axes of the parallel co-ordinates.

15. The article of manufacture of claim 13, wherein fragmenting the pair of axes further include instructions to:
    fragment a first axis of the corresponding segment into a finite number of bins, each bin representing the attributing continuous values associated with the continuous variable corresponding to the first axis;
    fragment a second axis of the corresponding segment into a finite number of bins, each bin representing the attributing continuous values associated with the continuous variable corresponding to the second axis; and
    generate the bi-variant bins by consolidating the bins from the first axis and the bins from the second axis.

16. The article of manufacture of claim 13, wherein generating the statistical visualization further include instructions to:
    generate a distribution of the tuples for each segment to represent a data flow between the pairs of axes corresponding to the segment;
    generate the distribution of tuples for the plurality of segments to represent a data flow for all the segments; and
    implement bi-variant plotting of the tuples for the plurality of segments corresponding to the parallel co-ordinates.

17. A computer system to generate a generate a visualization of parallel co-ordinates, comprising:
    a processor configured to read and execute instructions stored in one or more memory elements; and
    the one or more memory elements storing instructions related to—
        divide the parallel co-ordinates into a plurality of segments based upon one or more associated categorical variables, each segment including a pair of continuous variables represented as a pair of axes of the parallel co-ordinates;
        fragment the pairs of axes to generate one or more bi-variant bins including one or more continuous values corresponding to each fragment of the axes;
        query a backend database associated with the parallel co-ordinates to determine one or more aggregated tuples of continuous values between each bi-variant bin of the corresponding pair of axes, the aggregated tuples are determined by:
            determining a count of tuples corresponding to each bi-variant bin by aggregating corresponding number of continuous values;
            determining an aggregation of continuous values corresponding to each bi-variant bin by aggregating the corresponding continuous values; and storing the count of continuous values and the aggregation of continuous values as aggregated tuples; and generate a statistical visualization of the aggregated tuples between the bi-variant bins for the axes associated with the parallel co-ordinates on a computer generated user interface, the statistical visualization including a distribution of the tuples for the plurality of segments corresponding to the parallel co-ordinates.

18. The computer system of claim 17 further including:

a user interface component comprising —a user interface engine to trigger the statistical visualization, a parameter selection module to select a categorical value for analysis, and a parameter assignment module to assign the categorical variables and the continuous variables to the parallel co-ordinates;

an in-database aggregation component comprising—
   a query module to query the backend database and determine aggregated tuples of continuous values between the bi-variant bins of the corresponding pair of axes,
   a separation module to divide the parallel co-ordinates into segment and fragment the segments to generate the bi-variant bins, and
   an analysis module to generates a statistical visualization of the aggregated tuples; and a backend database comprising —an aggregation module to determine the aggregated tuples, a tuple storage module to store metadata associated with the tuples, and a bin storage module to store metadata associated with the fragmentation of the parallel co-ordinates.

* * * * *